(12) United States Patent
Coverston et al.

(10) Patent No.: US 9,138,180 B1
(45) Date of Patent: Sep. 22, 2015

(54) SENSOR ADAPTER CABLE

(75) Inventors: Ronald Coverston, Portola Hills, CA (US); Michael Lee, Aliso Viejo, CA (US)

(73) Assignee: Masimo Corporation, Irvine, CA (US)

( * ) Notice: Subject to any disclaimer, the term of this patent is extended or adjusted under 35 U.S.C. 154(b) by 1052 days.

(21) Appl. No.: 13/100,287

(22) Filed: May 3, 2011

Related U.S. Application Data

(60) Provisional application No. 61/330,586, filed on May 3, 2010.

(51) Int. Cl.
*A61B 5/1455* (2006.01)

(52) U.S. Cl.
CPC ......... *A61B 5/1455* (2013.01); *A61B 2562/222* (2013.01); *H01R 2201/12* (2013.01)

(58) Field of Classification Search
CPC .................... A61B 2562/08; A61B 2562/085; A61B 2652/222; A61B 2562/225; H01R 2201/12
USPC .................... 600/310, 322, 323, 344; 439/909
See application file for complete search history.

(56) References Cited

U.S. PATENT DOCUMENTS

| | | |
|---|---|---|
| 4,822,997 A | 4/1989 | Fuller et al. |
| 4,868,476 A | 9/1989 | Respaut |
| 4,890,306 A | 12/1989 | Noda |
| 4,942,877 A | 7/1990 | Sakai et al. |
| 4,960,128 A | 10/1990 | Gordon et al. |
| 4,964,408 A | 10/1990 | Hink et al. |
| 4,975,647 A | 12/1990 | Downer et al. |
| 4,996,975 A | 3/1991 | Nakamura |
| 5,041,187 A | 8/1991 | Hink et al. |
| 5,058,588 A | 10/1991 | Kaestle |
| 5,069,213 A | 12/1991 | Polczynski |
| 5,155,697 A | 10/1992 | Bunsen |
| 5,162,725 A | 11/1992 | Hodson et al. |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| 5,355,129 A | 10/1994 | Baumann |
| D353,195 S | 12/1994 | Savage et al. |

(Continued)

FOREIGN PATENT DOCUMENTS

| | | |
|---|---|---|
| DE | 3244695 C2 | 10/1985 |
| EP | 0469395 B1 | 2/1996 |

(Continued)

OTHER PUBLICATIONS

"Application Note 84 Use of Add-Only Memory for Secure Storage of Monetary Equivalent Data," Dallas Semiconductor, Jun. 22, 1999, in 5 pages.

(Continued)

*Primary Examiner* — Eric Winakur
(74) *Attorney, Agent, or Firm* — Knobbe Martens Olson & Bear LLP

(57) ABSTRACT

A sensor adapter cable provides medical personnel with the convenience of utilizing otherwise incompatible optical sensors with multiple blood parameter plug-ins to a physiological monitor, where the plug-ins each have keyed connectors that mechanically lock-out incompatible sensors in addition readers that poll sensor identification components in each sensor so as to electrically lock-out incompatible sensors.

16 Claims, 11 Drawing Sheets

(56) References Cited

U.S. PATENT DOCUMENTS

| | | |
|---|---|---|
| D353,196 S | 12/1994 | Savage et al. |
| 5,377,676 A | 1/1995 | Vari et al. |
| 5,383,874 A | 1/1995 | Jackson et al. |
| 5,400,267 A | 3/1995 | Denen et al. |
| D359,546 S | 6/1995 | Savage et al. |
| 5,425,362 A | 6/1995 | Siker et al. |
| 5,425,375 A | 6/1995 | Chin et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,487,386 A | 1/1996 | Wakabayashi et al. |
| 5,490,505 A | 2/1996 | Diab et al. |
| 5,494,043 A | 2/1996 | O'Sullivan et al. |
| 5,528,519 A | 6/1996 | Ohkura et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,603,323 A | 2/1997 | Pflugrath et al. |
| 5,615,672 A | 4/1997 | Braig et al. |
| 5,617,857 A | 4/1997 | Chader et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,651,780 A | 7/1997 | Jackson et al. |
| 5,658,248 A | 8/1997 | Klein et al. |
| 5,685,299 A | 11/1997 | Diab et al. |
| 5,720,293 A | 2/1998 | Quinn et al. |
| D393,830 S | 4/1998 | Tobler et al. |
| 5,742,718 A | 4/1998 | Harman et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,779,630 A | 7/1998 | Fein et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,121 A | 11/1998 | Enomoto et al. |
| 5,830,131 A | 11/1998 | Caro et al. |
| 5,833,618 A | 11/1998 | Caro et al. |
| 5,850,443 A | 12/1998 | Van Oorschot et al. |
| 5,860,099 A | 1/1999 | Milios et al. |
| 5,860,919 A | 1/1999 | Kiani-Azarbayjany et al. |
| 5,890,929 A | 4/1999 | Mills et al. |
| 5,900,632 A | 5/1999 | Sterling et al. |
| 5,904,654 A | 5/1999 | Wohltmann et al. |
| 5,919,134 A | 7/1999 | Diab |
| 5,934,925 A | 8/1999 | Tobler et al. |
| 5,939,609 A | 8/1999 | Knapp et al. |
| 5,940,182 A | 8/1999 | Lepper, Jr. et al. |
| 5,987,343 A | 11/1999 | Kinast |
| 5,991,355 A | 11/1999 | Dahlke |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,132,363 A | 10/2000 | Freed et al. |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,163,715 A | 12/2000 | Larsen et al. |
| 6,165,005 A | 12/2000 | Mills et al. |
| 6,165,173 A | 12/2000 | Kamdar et al. |
| 6,175,752 B1 | 1/2001 | Say et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,237,604 B1 | 5/2001 | Burnside et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,266,551 B1 | 7/2001 | Osadchy et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,295,330 B1 | 9/2001 | Skog et al. |
| 6,298,255 B1 | 10/2001 | Cordero et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,336,900 B1 | 1/2002 | Alleckson et al. |
| 6,339,715 B1 | 1/2002 | Bahr et al. |
| 6,343,224 B1 | 1/2002 | Parker |
| 6,349,228 B1 | 2/2002 | Kiani et al. |
| 6,351,658 B1 * | 2/2002 | Middleman et al. .......... 600/331 |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,490,684 B1 | 12/2002 | Fenstemaker et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,645,142 B2 | 11/2003 | Braig et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,676,600 B1 | 1/2004 | Conero et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |

(56) References Cited

U.S. PATENT DOCUMENTS

| | | |
|---|---|---|
| RE38,476 E | 3/2004 | Diab et al. |
| 6,699,194 B1 | 3/2004 | Diab et al. |
| 6,708,049 B1 | 3/2004 | Berson et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-All |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,606,861 B2 | 10/2009 | Killcommons et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |

(56) References Cited

U.S. PATENT DOCUMENTS

| | | |
|---|---|---|
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |

(56) References Cited

U.S. PATENT DOCUMENTS

| | | |
|---|---|---|
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 2002/0068858 A1 | 6/2002 | Braig et al. |
| 2002/0095077 A1 | 7/2002 | Swedlow et al. |
| 2002/0095078 A1 | 7/2002 | Mannheimer et al. |
| 2009/0247984 A1 | 10/2009 | Lamego et al. |
| 2009/0275844 A1 | 11/2009 | Al-Ali |
| 2009/0299157 A1 | 12/2009 | Telfort et al. |
| 2010/0004518 A1 | 1/2010 | Vo et al. |
| 2010/0030040 A1 | 2/2010 | Poeze et al. |
| 2010/0261979 A1 | 10/2010 | Kiani |
| 2010/0317936 A1 | 12/2010 | Al-Ali et al. |
| 2011/0001605 A1 | 1/2011 | Kiani et al. |
| 2011/0082711 A1 | 4/2011 | Poeze et al. |
| 2011/0105854 A1 | 5/2011 | Kiani et al. |
| 2011/0208015 A1 | 8/2011 | Welch et al. |
| 2011/0209915 A1 | 9/2011 | Telfort et al. |
| 2011/0213212 A1 | 9/2011 | Al-Ali |
| 2011/0230733 A1 | 9/2011 | Al-Ali |
| 2011/0237911 A1 | 9/2011 | Lamego et al. |
| 2012/0059267 A1 | 3/2012 | Lamego et al. |
| 2012/0116175 A1 | 5/2012 | Al-Ali et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0227739 A1 | 9/2012 | Kiani |
| 2012/0265039 A1 | 10/2012 | Kiani |
| 2012/0283524 A1 | 11/2012 | Kiani et al. |
| 2012/0286955 A1 | 11/2012 | Welch et al. |
| 2012/0296178 A1 | 11/2012 | Lamego et al. |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0041591 A1 | 2/2013 | Lamego |
| 2013/0045685 A1 | 2/2013 | Kiani |
| 2013/0046204 A1 | 2/2013 | Lamego et al. |
| 2013/0060108 A1 | 3/2013 | Schurman et al. |
| 2013/0060147 A1 | 3/2013 | Welch et al. |
| 2013/0079610 A1 | 3/2013 | Al-Ali |
| 2013/0096405 A1 | 4/2013 | Garfio |
| 2013/0096936 A1 | 4/2013 | Sampath et al. |
| 2013/0109935 A1 | 5/2013 | Al-Ali et al. |
| 2013/0162433 A1 | 6/2013 | Muhsin et al. |
| 2013/0190581 A1 | 7/2013 | Al-Ali et al. |
| 2013/0197328 A1 | 8/2013 | Diab et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0274571 A1 | 10/2013 | Diab et al. |
| 2013/0296672 A1 | 11/2013 | O'Neil et al. |
| 2013/0317370 A1 | 11/2013 | Dalvi et al. |
| 2013/0324808 A1 | 12/2013 | Al-Ali et al. |
| 2013/0331670 A1 | 12/2013 | Kiani |
| 2013/0338461 A1 | 12/2013 | Lamego et al. |
| 2014/0012100 A1 | 1/2014 | Al-Ali et al. |
| 2014/0025306 A1 | 1/2014 | Weber et al. |
| 2014/0034353 A1 | 2/2014 | Al-Ali et al. |
| 2014/0051952 A1 | 2/2014 | Reichgott et al. |
| 2014/0051953 A1 | 2/2014 | Lamego et al. |
| 2014/0051954 A1 | 2/2014 | Al-Ali et al. |
| 2014/0058230 A1 | 2/2014 | Abdul-Hafiz et al. |
| 2014/0066783 A1 | 3/2014 | Kiani et al. |
| 2014/0077956 A1 | 3/2014 | Sampath et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0125495 A1 | 5/2014 | Al-Ali |
| 2014/0127137 A1 | 5/2014 | Bellott et al. |
| 2014/0128696 A1 | 5/2014 | Al-Ali |
| 2014/0128699 A1 | 5/2014 | Al-Ali et al. |
| 2014/0129702 A1 | 5/2014 | Lamego et al. |
| 2014/0135588 A1 | 5/2014 | Al-Ali et al. |
| 2014/0142401 A1 | 5/2014 | Al-Ali et al. |
| 2014/0142402 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0200420 A1 | 7/2014 | Al-Ali |
| 2014/0200422 A1 | 7/2014 | Weber et al. |
| 2014/0206963 A1 | 7/2014 | Al-Ali |
| 2014/0213864 A1 | 7/2014 | Abdul-Hafiz et al. |
| 2014/0243627 A1 | 8/2014 | Diab et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0288400 A1 | 9/2014 | Diab et al. |
| 2014/0296664 A1 | 10/2014 | Bruinsma et al. |
| 2014/0303520 A1 | 10/2014 | Telfort et al. |
| 2014/0309506 A1 | 10/2014 | Lamego et al. |
| 2014/0309559 A1 | 10/2014 | Telfort et al. |
| 2014/0316228 A1 | 10/2014 | Blank et al. |
| 2014/0323825 A1 | 10/2014 | Al-Ali et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0343436 A1 | 11/2014 | Kiani |
| 2015/0018650 A1 | 1/2015 | Al-Ali et al. |

FOREIGN PATENT DOCUMENTS

| | | |
|---|---|---|
| EP | 0417447 B1 | 10/1997 |
| EP | 0606356 B1 | 6/1998 |
| EP | 0734221 B1 | 7/1998 |
| JP | H06-178776 | 6/1994 |
| JP | H07-391 | 1/1995 |
| JP | H07-171089 | 7/1995 |
| JP | H07-171090 | 7/1995 |
| JP | 2001-504256 | 3/2001 |
| WO | WO 93/06776 | 4/1993 |

(56) References Cited

FOREIGN PATENT DOCUMENTS

| WO | WO 97/29678 | 8/1997 |
| WO | WO 97/029710 | 8/1997 |

OTHER PUBLICATIONS

Dallas Semiconductor Corp: DS2430A Announcement, retrieved Jun. 10, 1998, in 2 pages. <https://web.archive.org/web/19980610045525/http://dalsemi.com/News_Center/New_Products/1996/2430a.html>.

Favennec, J.M. "Smart sensors in industry." J. Phys. E: Sci. Instrum. 20(9): Sep. 1987, pp. 1087-1090.

Jones, K.L., et al. "A Protocol for Automatic Sensor Detection and Identification in a Wireless Biodevice Network," IEEE, Jun. 1998, 6 pages.

"Medical." 50 Ways to Touch Memory. 3rd ed. Dallas: Dallas Semiconductor Corporation, Aug. 1994: pp. 24-25. Print.

Subramanian, S., et al. "Design for Constraint Violation Detection in Safety-Critical Systems," IEEE, Nov. 1998: pp. 1-8.

US 8,845,543, 09/2014, Diab et al. (withdrawn)

* cited by examiner

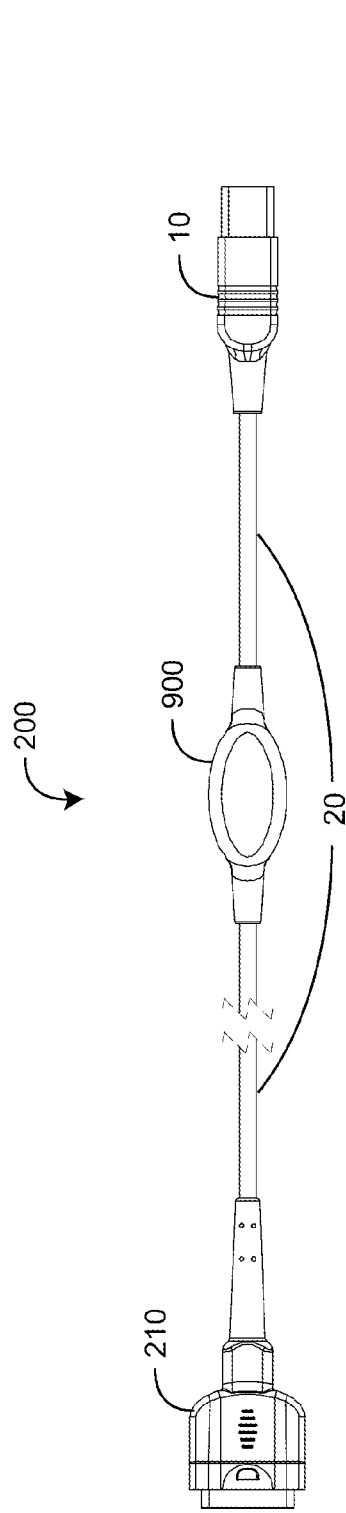
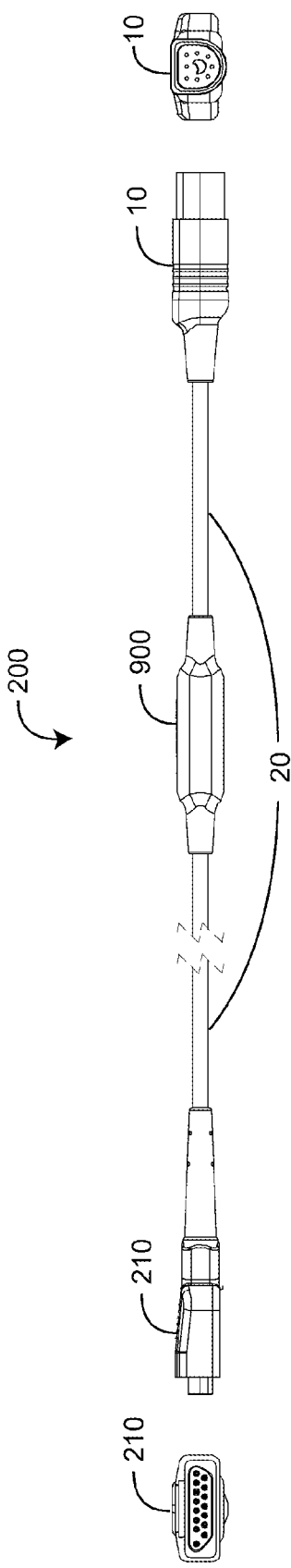
FIG. 2A
FIG. 2B

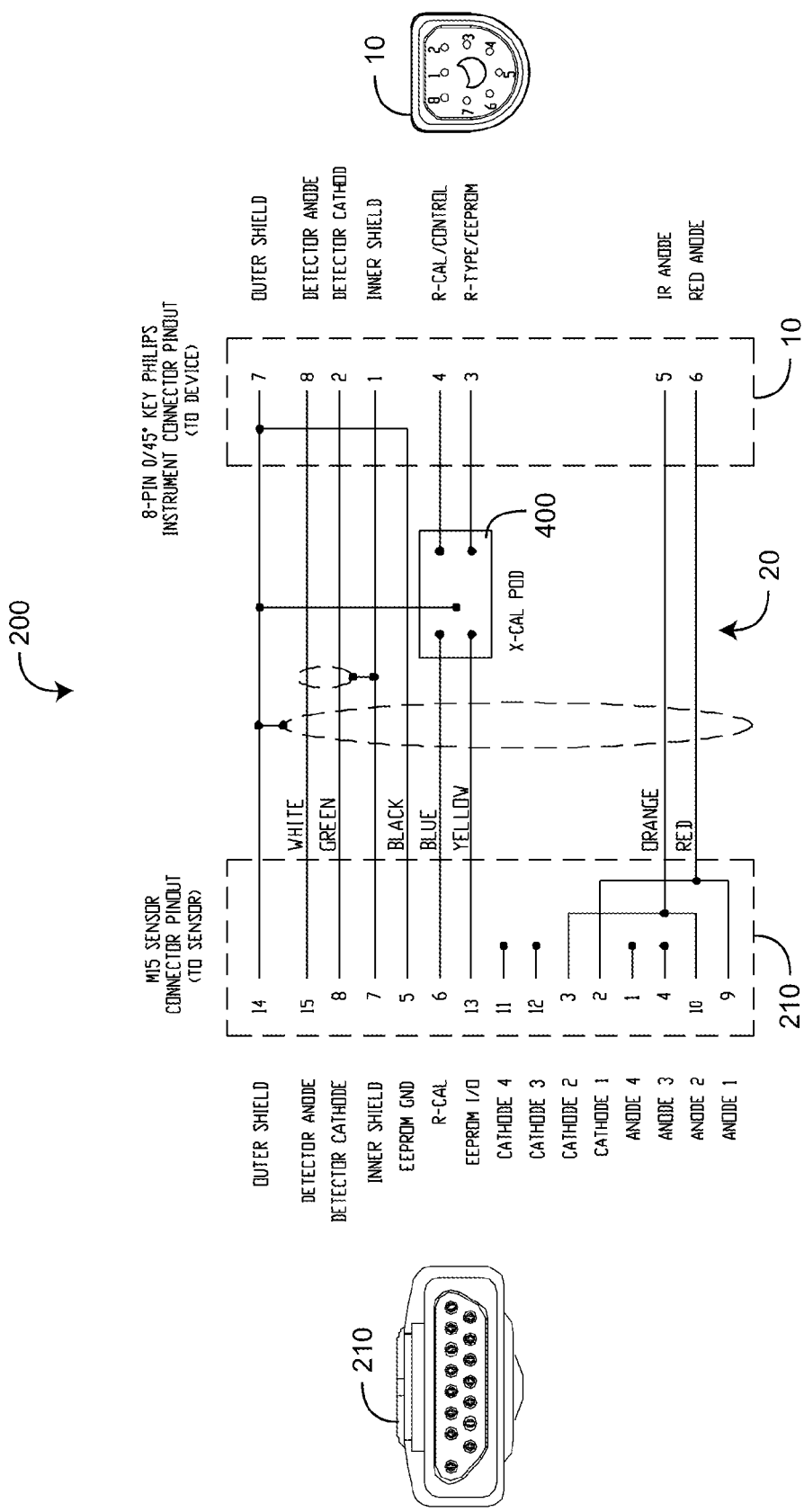

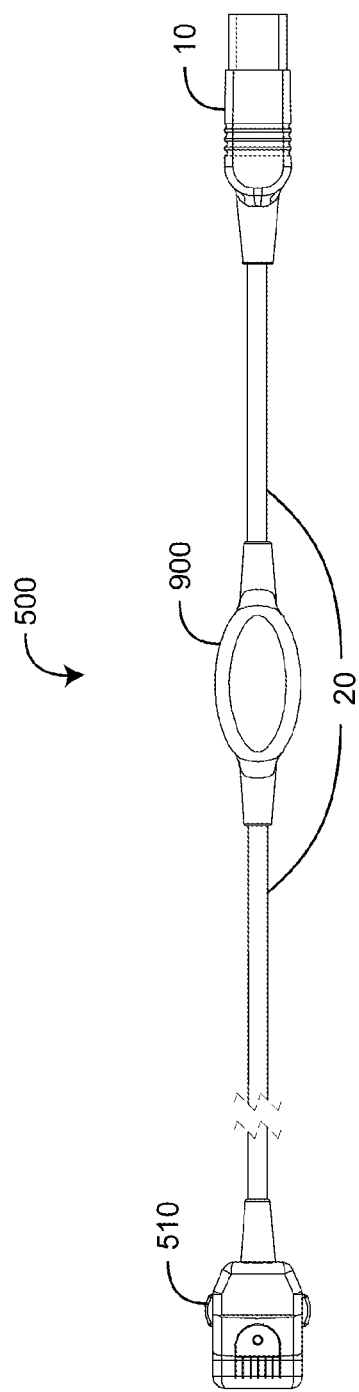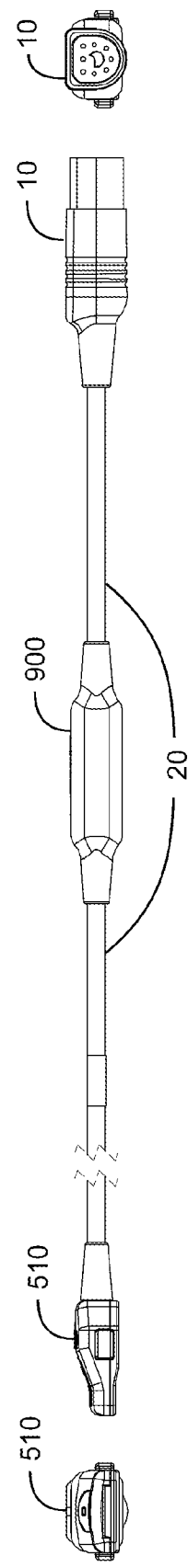
FIG. 5A
FIG. 5B

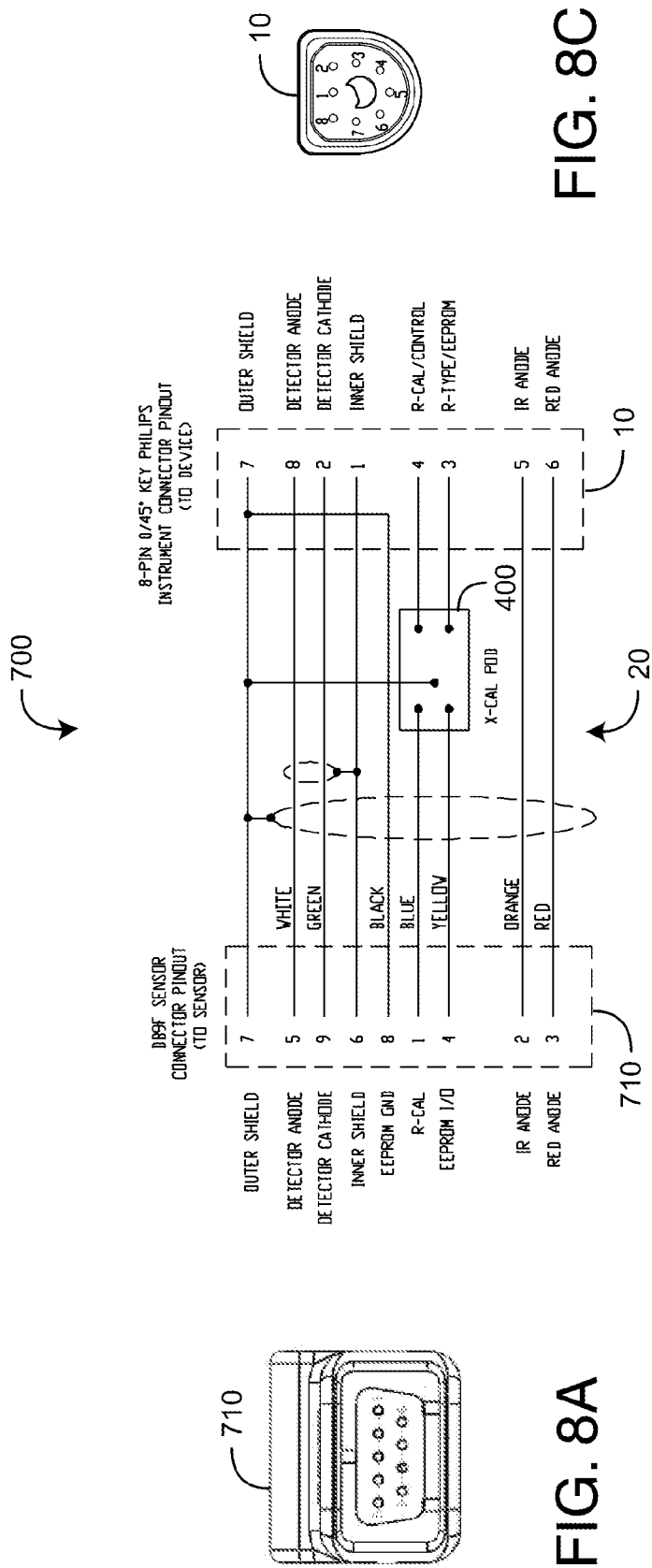

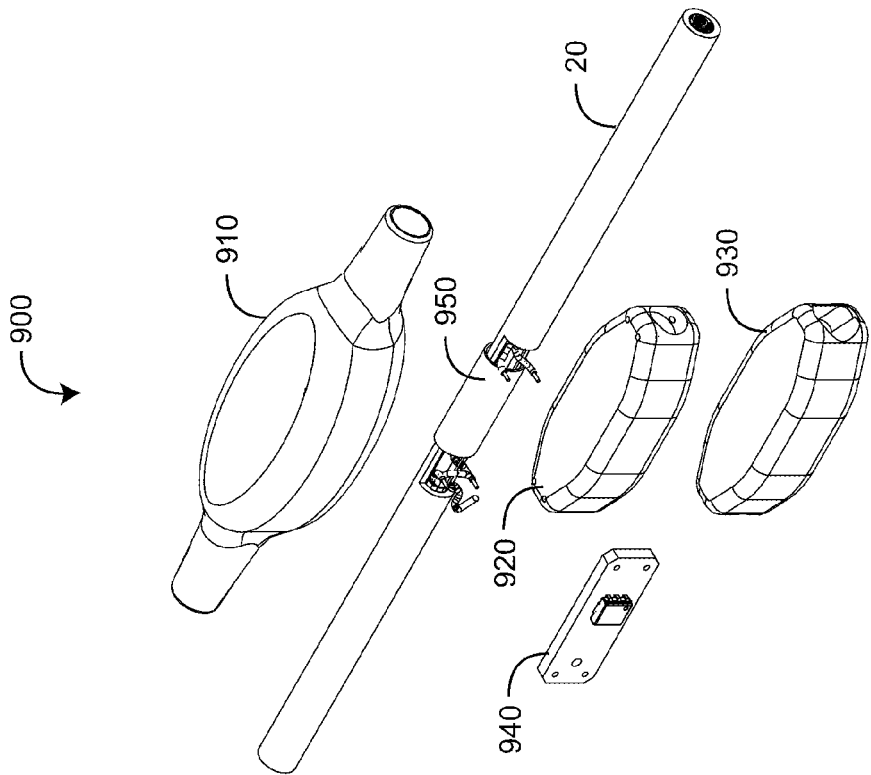
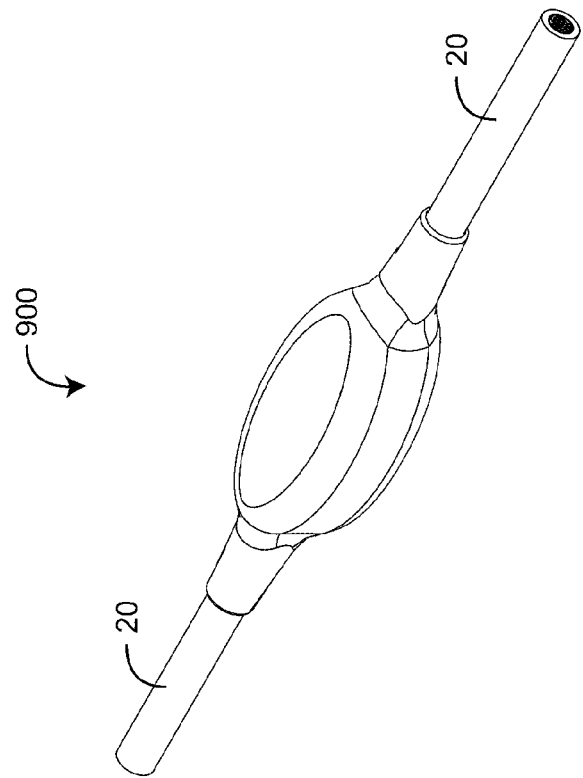

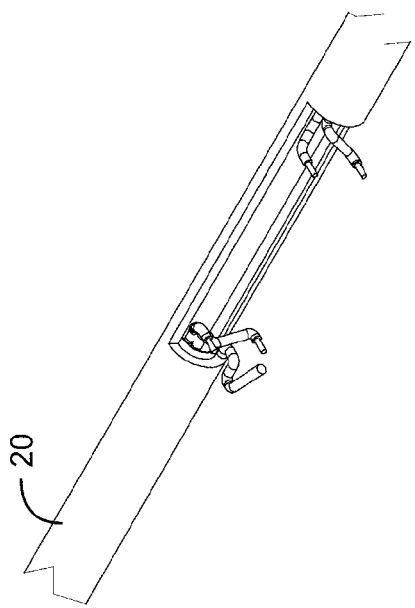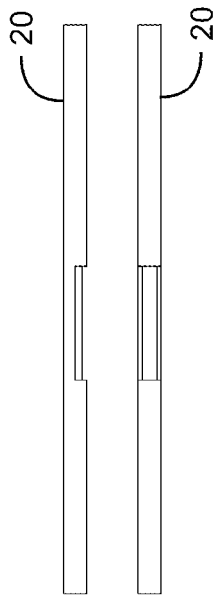
FIG. 10A
FIG. 10B
FIG. 10D
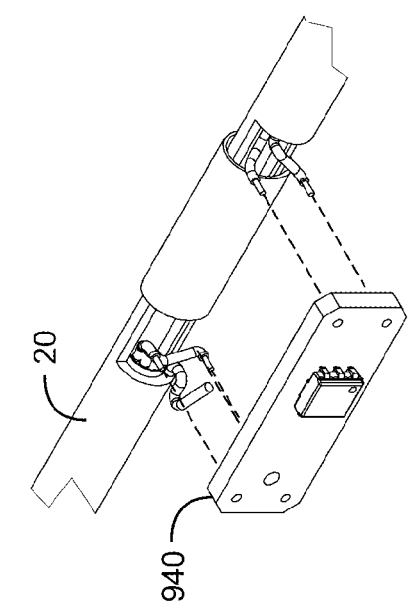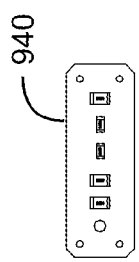
FIG. 10C

SENSOR ADAPTER CABLE

PRIORITY CLAIM TO RELATED PROVISIONAL APPLICATIONS

The present application claims priority benefit under 35 U.S.C. §119(e) to U.S. Provisional Patent Application Ser. No. 61/330,586 filed May 3, 2010, titled Sensor Adapter Cable; the above-cited provisional patent application is hereby incorporated by reference herein.

BACKGROUND OF THE INVENTION

Pulse oximetry systems for measuring constituents of circulating blood have gained rapid acceptance in a wide variety of medical applications, including surgical wards, intensive care and neonatal units, general wards, home care, physical training, and virtually all types of monitoring scenarios. A pulse oximetry system generally includes an optical sensor applied to a patient, a monitor for processing sensor signals and displaying results and a patient cable electrically interconnecting the sensor and the monitor. The monitor may be specific to pulse oximetry or may be a multi-parameter monitor that has a pulse oximetry plug-in. A pulse oximetry sensor has light emitting diodes (LEDs), typically one emitting a red wavelength and one emitting an infrared (IR) wavelength, and a photodiode detector. The emitters and detector are typically attached to a finger, and the patient cable transmits drive signals to these emitters from the monitor. The emitters respond to the drive signals to transmit light into the fleshy fingertip tissue. The detector generates a signal responsive to the emitted light after attenuation by pulsatile blood flow within the fingertip. The patient cable transmits the detector signal to the monitor, which processes the signal to provide a numerical readout of pulse oximetry parameters such as oxygen saturation ($SpO_2$) and pulse rate.

SUMMARY OF THE INVENTION

A sensor adapter cable provides medical personnel with the convenience of utilizing otherwise incompatible sensors with multiple $SpO_2$ monitors or monitor plug-ins. For example, each monitor plug-in may have a keyed connector that mechanically locks-out incompatible sensors. Further, each sensor may have sensor identification (ID) components that can be read by a pulse oximetry monitor or monitor plug-in so as to electrically lock-out incompatible sensors. The sensor adapter cable advantageously allows the interconnection of these otherwise incompatible devices. In an embodiment, a sensor adapter cable allows the use of any of a Masimo sensor with a ProCal ID, a Masimo sensor with an EEPROM ID and a Nellcor/Philips sensor with an R-cal ID with either of a Masimo SET plug-in or a Philips FAST-SpO2 plug-in to a Philips IntelliVue™ monitor, all available from Philips Medical Systems, Andover, Mass.

A sensor adapter cable has both a mechanical and an electrical interface to a monitor plug-in so as to provide multiple sensor compatibility. In an embodiment, a dual key 8-pin D-shape connector (D8) at one end of an adapter cable provides mechanical compatibility with two-types of plug-in input connectors, as described in U.S. patent application Ser. No. 11/238,634 (Pub No. US2006/0073719 A1) titled Multiple Key Position Plug filed Sep. 29, 2005 and incorporated by reference herein. Further, a family of sensor adapter cables has sensor connector configurations that include MC8, M15 and DB9 connectors, as shown and described below.

The limited pins available on a D8 connector require sharing of pins to accommodate various sensor ID components. For example, an EEPROM sensor ID and a R-cal resistor sensor ID may need to share the same D8 pin. Such an approach, however, creates the potential for the EEPROM to effect the R-cal measurement in Philips FAST equipped devices and for the R-cal voltage drop to effect the ability of Masimo SET equipped devices to read the EEPROM.

An 8-pin dual-key cable which is capable of working correctly with any combination of Philips or Masimo SET equipped SpO2 plug-ins requires the connection of the proper ID component(s) to the SpO2 plug-ins while at the same time electrically disconnecting components that are not used or that could potentially interfere with the connected SpO2 technology. Further, this solution cannot impact the ability of each of the SpO2 technologies to operate correctly across its entire range of sensors and accessories.

One aspect of a sensor adapter cable provides medical personnel with the convenience of utilizing otherwise incompatible optical sensors with multiple blood parameter plug-ins to a physiological monitor. The plug-ins each have keyed connectors that mechanically lock-out incompatible sensors in addition to readers that poll sensor identification components in each sensor so as to electrically lock-out incompatible sensors. The sensor adapter cable has a sensor connector, a plug-in connector, an interconnection cable and a pod. The sensor connector mechanically connects to a predetermined sensor and electrically communicates with sensor electrical elements within the predetermined sensor. The plug-in connector mechanically connects to a predetermined plug-in and electrically communicates with lug-in electrical elements within the predetermined plug-in. An interconnection cable mechanically attaches between and provides electrical communications between the sensor connector and the plug-in connector. A pod is incorporated within the interconnecting cable that electrically interfaces the sensor connector to the plug-in connector.

In various embodiments, the pod has a cut in the interconnection cable that exposes cable wire ends. A circuit board is spliced to the cable wires end. A pre-mold encapsulates the cut, the circuit board, and the cable wire end, and an overmold envelopes the pre-mode so as to define the pod. The circuit board comprises a first switch that, when closed, connects a resistor ID on the circuit board to the plug-in connector so as to enable a first plug-in attached to the plug-in connector to communicate with a sensor attached to the sensor connector. The circuit board also comprises a second switch that, when closed, connects an EEPROM ID on the circuit board to the plug-in connector so as to enable a second plug-in attached to the plug-in connector to communicate with a sensor attached to the sensor connector. The sensor adapter cable disconnects the resistor ID and the EEPROM ID when the first switch and the second switch are both open. The first switch may incorporate an n-channel MOSFET that turns on in response to a positive control signal from the first plug-in so as to switch in the resistor ID. The second switch may incorporate a p-channel MOSFET that turns on in response to a negative control signal from the second plug-in so as to switch in the EEPROM ID.

Another aspect of a sensor adapter cable is a method of interfacing any of multiple physiological monitor plug-ins to any of multiple optical sensors. An interface cable has a sensor connector on a first end and a plug-in connector on a second end. Resistive and memory IDs are incorporated within the cable. A sensor ID read signal is asserted at the plug-in connector. A particular one of the IDs is presented to the plug-in connector in response to the read signal. In various embodiments, unselected IDs are isolated from the plug-in connector and the selected ID. Switches are integrated with the IDs and are responsive to the read signal so as to connect the selected ID and disconnect the remaining IDs. A first switch is closed and a second switch is opened so as to select either a resistive ID or a memory ID. Both the first switch and the second switch are opened so that the sensor adapter cable functions as a patient cable. A circuit board with the switches and IDs is spliced between a portion of the interface cable conductors. The circuit board is encapsulated into a calibration pod portion of the interface cable.

A further aspect of a sensor adapter cable is a plug-in connector means for connecting to a plug-in module for a physiological monitor. A sensor connector means connects to an optical sensor. An interface cable mechanically and electrically interconnects the plug-in connector means and the sensor connector means. A pod means is integrated with the interface cable for allowing sensors to connected to and be recognized by the plug-in module. In various embodiments, the pod means comprises a circuit board means for splicing sensor IDs into the interface cable. A switching means selectively activates and isolates the sensor IDs so that only a single sensor ID is presented to the plug-in connector. A control means is in communications with the plug-in connector means for making the switching means responsive to a ID read signal from the plug-in module. The pod means further comprises an encapsulation means for enclosing the circuit board means within the pod means, where an encapsulations means embodiment comprises a premold of at least one of an epoxy, HDPE and PVC and an overmold of medical grade PVC.

DESCRIPTION OF THE DRAWINGS

FIGS. 2A-B are top, side and end views of a sensor adapter cable embodiment employing a M15 sensor connector and a D8 plug-in connector;

FIGS. 3A-C are a M15 connector end view; a cable schematic and a D8 connector end view, respectively;

FIGS. 5A-B are top, side and end views of a sensor adapter cable embodiment employing a MC8 sensor connector and a D8 plug-in connector;

FIGS. 8A-C are a DB9 connector end view; a cable schematic and a D8 connector end view, respectively;

FIGS. 9A-B are a perspective view and an exploded perspective view, respectively, of a sensor adapter cable pod;

FIGS. 10A-B are a perspective views of a sensor adapter circuit board and cable assembly;

FIG. 10C is a cable-side view of a sensor adapter circuit board;

FIG. 10D are cable prep top and side views; and

DETAILED DESCRIPTION OF THE PREFERRED EMBODIMENTS

Figure 1:
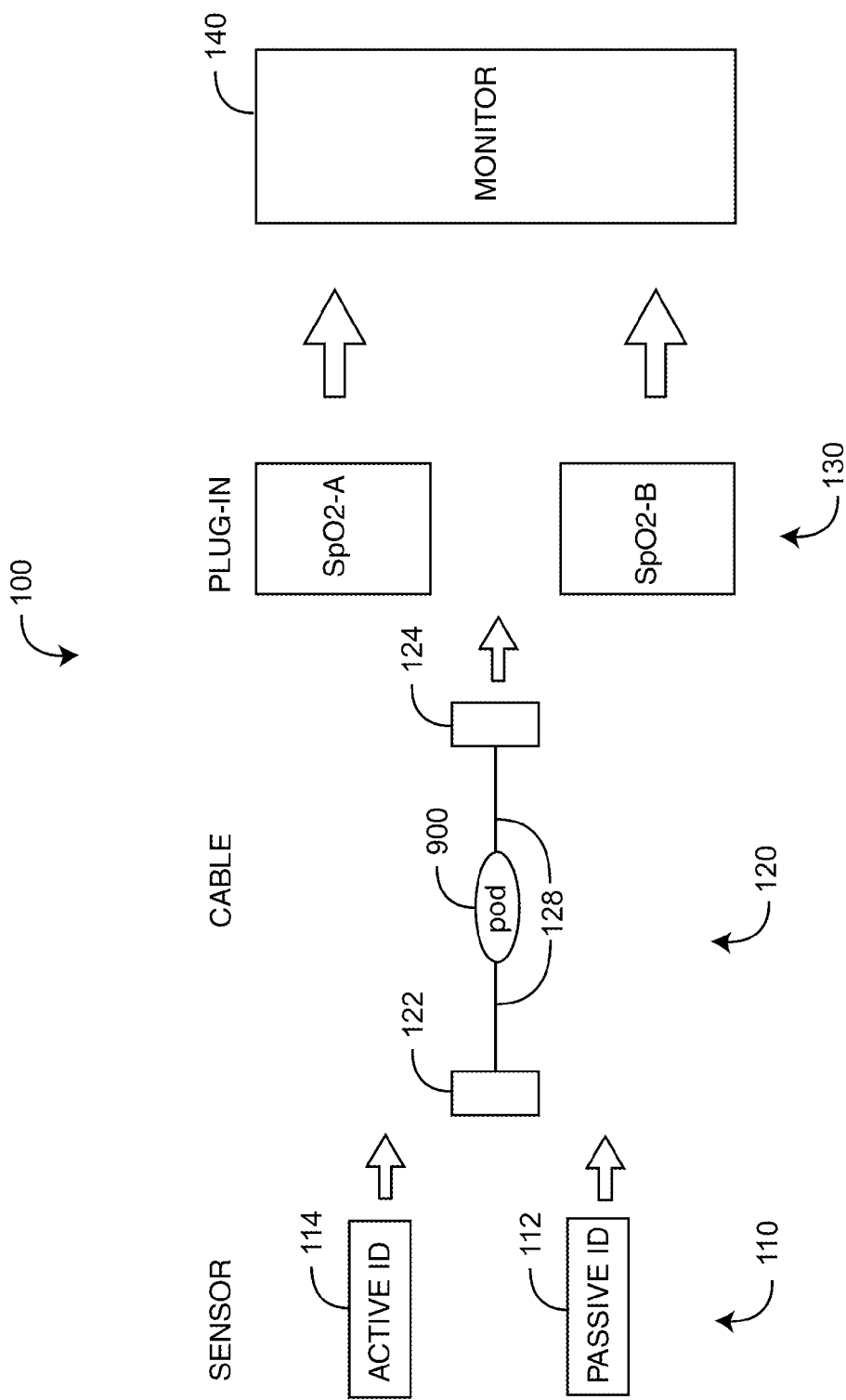
FIG. 1 is a general block diagram of a physiological parameter monitoring system that incorporates a sensor adapter cable.

FIG. 1 illustrates a physiological parameter monitoring system 100 that incorporates a sensor adapter cable 120 or a family of sensor adapter cables so as to interconnect various sensors 110 with parameter processing plug-ins 130 to a physiological monitor 140. The sensors 110 include various types and configurations of optical devices as described above. Sensors typically have ID components that identify the sensor to a plug-in 130 so as to insure compatibility. Examples of ID components include an active component ID 114, such as a memory, or a passive component ID 112, such as one or more resistors having a specified range of values. In a particular embodiment, an active component ID 114 includes an EEPROM and a passive component ID 112 includes a ProCal resistor (Masimo) or an R-cal resistor (Philips/Nellcor).

Also shown in FIG. 1, a sensor adapter cable 120 has a sensor connector 122, a plug-in connector 124, a pod 900 and an interconnecting cable 128. The sensor connector 122 mechanically and electrically interfaces to one or more sensors 112, 114. The plug-in connector 124 interfaces to one or more plug-ins 130. The plug-ins 130, in turn, mechanically and electrically connect with a physiological monitor 140. The sensors 110 provide sensor signals to the plug-ins, which are used to calculate oxygen saturation (SpO2) and pulse rate among other parameters. The monitor 140 controls the plug-in operating modes and displays the parameter calculations accordingly. In an embodiment, the plug-ins are any of Masimo® SET® modules (Masimo Corporation, Irvine, Calif.) or Philips FAST-SpO2 modules, all available from Philips Medical Systems, Andover, Mass. In an embodiment, the physiological monitor is any of various IntelliVue™ monitors also available from Philips. The sensor connector and/or the plug-in connector can be any of various D8, M15, MC8 and DB9 connectors to name a few.

FIGS. 2A-B illustrate a sensor adapter cable embodiment 200 employing a M15 sensor connector 210 and a D8 plug-in connector 10. A cable 20 interconnects the sensor connector 210 and the plug-in connector 10. A pod 900 integrated with the cable 20 contains a sensor adapter circuit 400 (FIG. 4) that insures electrical compatibility between a passive and an active ID 110 (FIG. 1) and a particular plug-in 130 (FIG. 1).

FIGS. 3A-C further illustrate a sensor adapter cable embodiment 200, showing the respective pinouts of the M15 connector 210 and the D8 connector 10. Also shown are the corresponding cable 20 color-coded wires, inner shield and outer shield. Further shown is a sensor adapter circuit 400 and its connections relative to the connectors 10, 210 and cable 20 wires.

Figure 4:
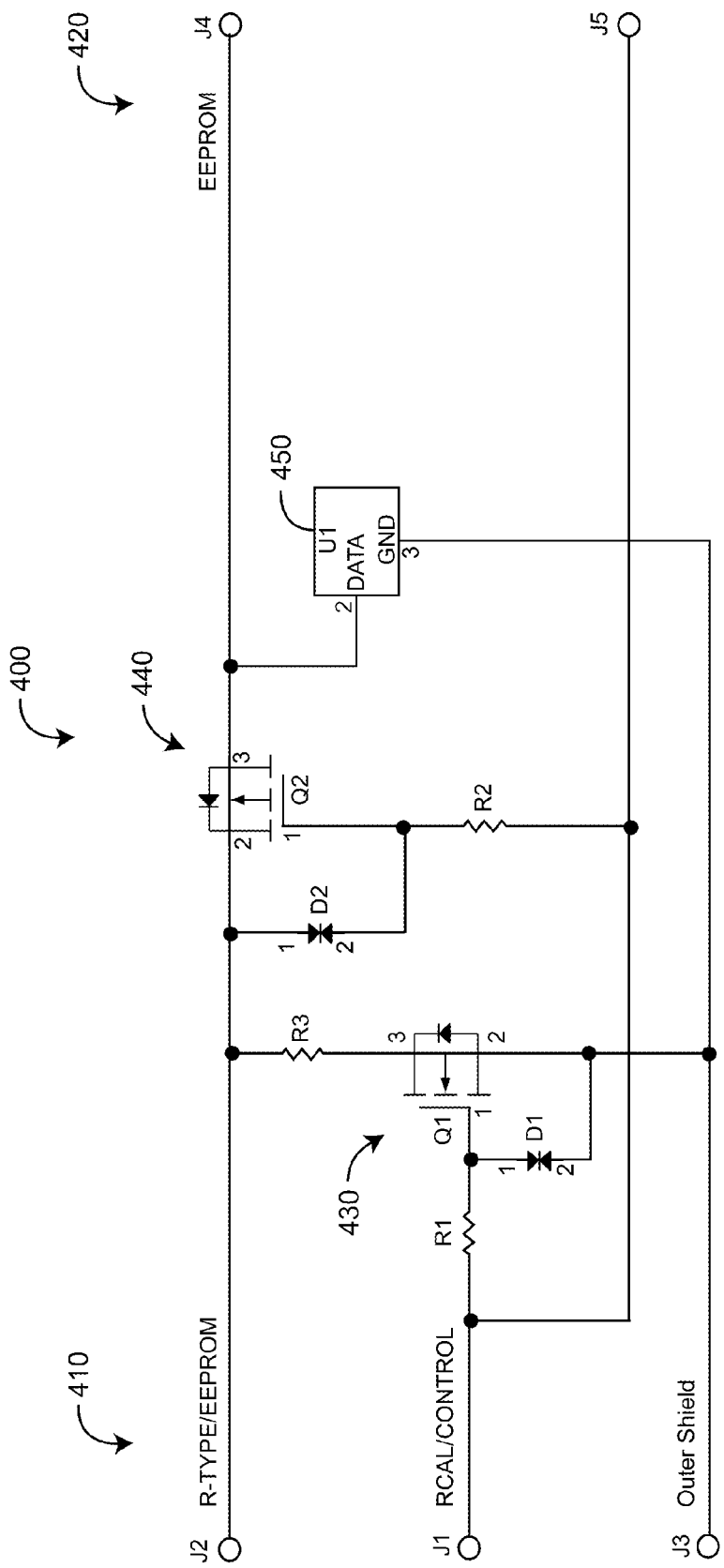
FIG. 4 is a detailed schematic of a sensor adapter circuit.

FIG. 4 illustrates the sensor adapter circuit 400 having plug-in connections 410 and sensor connections 420. The plug-in connections 410 (J1, J2, J3) connect to the plug-in connector 10 (FIGS. 2-3, 5-6, 7-8). The sensor connections 420 (J4, J5) connect to the sensor connector 210 (FIGS. 2-3); 510 (FIG. 5-6) or 710 (FIGS. 7-8). Table 1 below defines the signal names and associated connections to the plug-in connector pins.

TABLE 1

Adapter Circuit and Plug-in Connector Pinouts

| Signal Name | Reference Designation | Plug-in Connector Pin # |
|---|---|---|
| R-TYPE/EEPROM | J2 | 3 |
| RCAL/CONTROL | J1 | 4 |
| OUTER SHIELD | J3 | 7 |

The switch components 430, 440 used in this design (Si2312 and Si2351 or equivalents) are high impedance MOSFET devices that have no impact on R-cal and R-TYPE resistor measurements due to the fact that the MOSFET gates do not require current to activate. When the cable is connected to a Philips FAST equipped device, the RCAL/CONTROL signal will be a positive voltage. The RCAL/CONTROL voltage is 2.9V without a sensor connected and can be as low as 1.1V with the minimum value RCAL resistor of 6.04 KΩ. This is understood to represent the entire range for the RCAL/CONTROL voltage. When the cable is connected to a Masimo XCaI capable SpO2 module, a negative voltage will be applied to RCAL/CONTROL signal. This will turn on Q2 and turn off Q1 which will allow the Masimo system to read the EEPROM contents. Table 2, below, describes how the switches (Q1, Q2) operate.

TABLE 2

Adapter Circuit Switch Truth Table

| SpO2 Module | RCAL/ Control Signal | Switch Q1 | Switch Q2 | Comments |
|---|---|---|---|---|
| Philips FAST | Positive voltage | Closed | Open | Philips FAST module can measure RCAL and R-TYPE resistors |
| Masimo ProCal Technology | Open (No driving voltage) | Open (Don't care) | Open (Don't care) | Same as patient cable |
| Masimo XCal Technology | Negative voltage | Open | Closed | Masimo board will read EEPROM; negative voltage will be supplied by the Masimo board |

The n-channel transistor (Q1) 430 was chosen with a very low turn-on threshold (0.85V max) so that it is guaranteed to turn on and switch in the R-TYPE resistor even at the lowest RCAL/CONTROL voltage of 1.1V. The on-resistance of the FET is so low (less than 100 mΩ) that it will not affect the measured R-TYPE resistor value. At the same time, the p-channel FET (Q2) 440 will be turned off since the gate-to-source voltage (Vgs) will be positive. Even in the worst possible case, the Vgs will be −0.3V which is not low enough to turn-on the p-channel device. The minimum turn-on threshold for the p-channel is −0.6V. The purpose of resistors R1 and R2 and ESD protection diodes D1 and D2 are to protect the MOSFET devices. This sensor adapter embodiment ensures proper operation and ample margin in all possible combinations of sensor and device types and therefore meets the design requirements necessary to allow Masimo SET or Philips FAST systems to work correctly with a dual key D8 connector capable of plugging into either type of system.

Resistor R3 of FIG. 4 is a passive ID element on the sensor adapter circuit 400. U1 450 is an EEPROM and is an active ID element on the sensor adapter circuit 400.

FIGS. 5A-B illustrate a sensor adapter cable embodiment 500 employing a MC8 sensor connector 510 and a D8 plug-in connector 10. A cable 20 interconnects the sensor connector 510 and the plug-in connector 10. A pod 900 integrated with the cable 20 contains a sensor adapter circuit 400 (FIG. 4) that insures electrical compatibility between a passive and an active ID 110 (FIG. 1) and a particular plug-in 130 (FIG. 1).

Figures 6A, 6B, 6C:
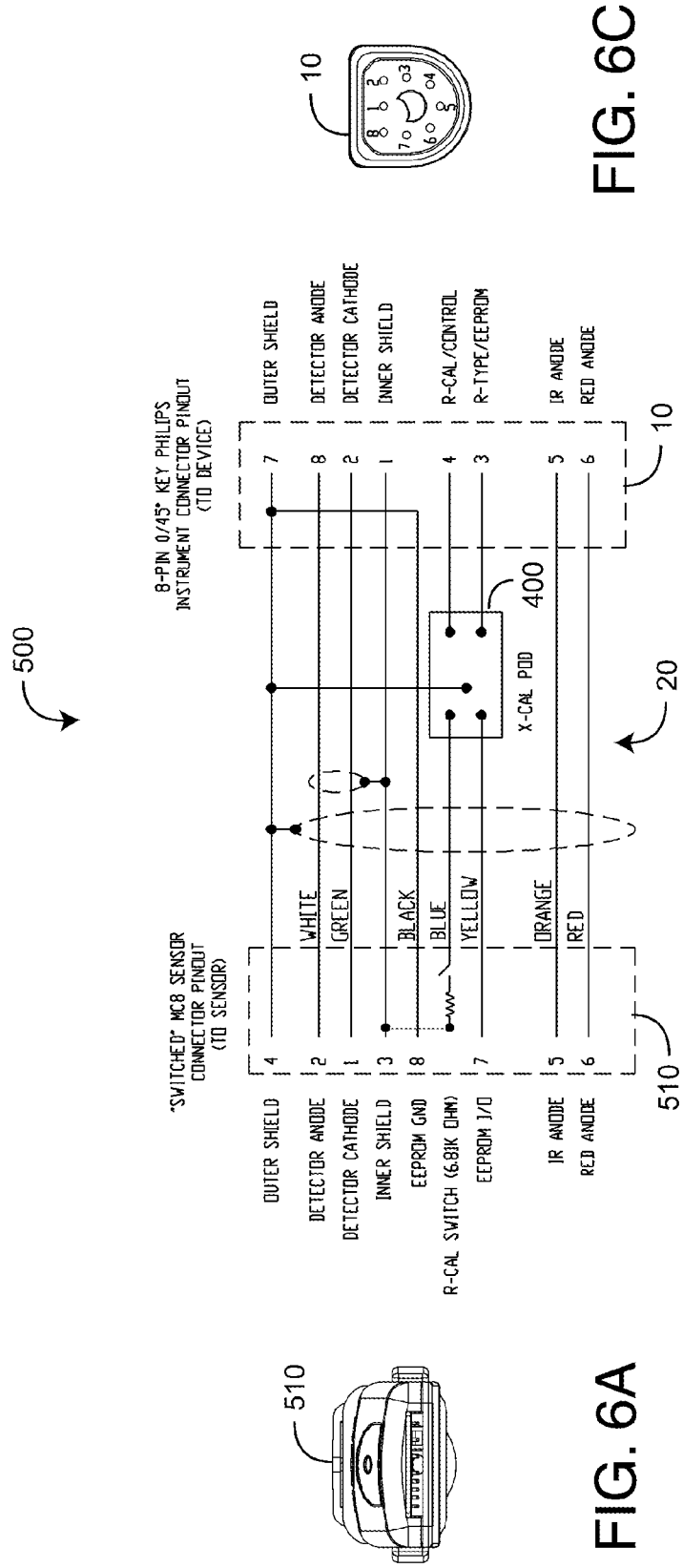
FIGS. 6A-C are a MC8 connector end view; a cable schematic and a D8 connector end view, respectively.

FIGS. 6A-C further illustrate a sensor adapter cable embodiment 500, showing the respective pinouts of the MC8 connector 510 and the D8 connector 10. Also shown are the corresponding cable 20 color-coded wires, inner shield and outer shield. Further shown are the sensor adapter circuit 400 connections relative to the connectors 10, 510 and cable 20 wires.

Figure 7A:
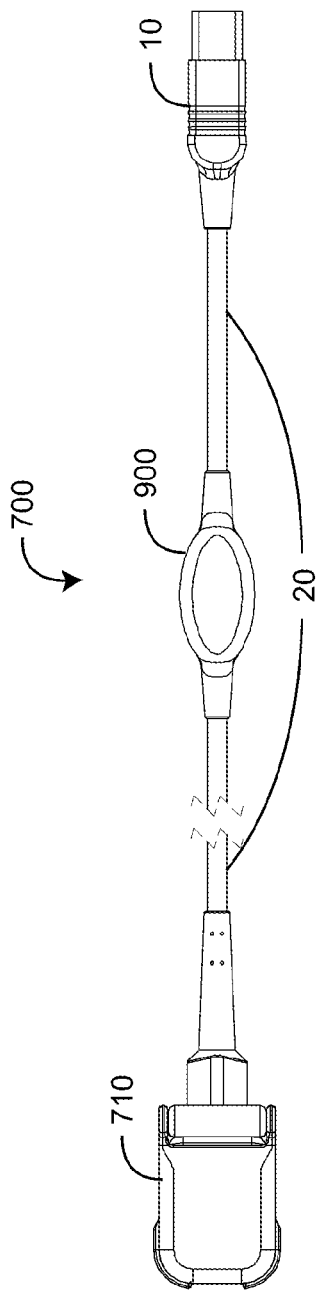
FIGS. 7A-B are top, side and end views of a sensor adapter cable embodiment employing a DB9 sensor connector and a D8 plug-in connector.
Figure 7B:
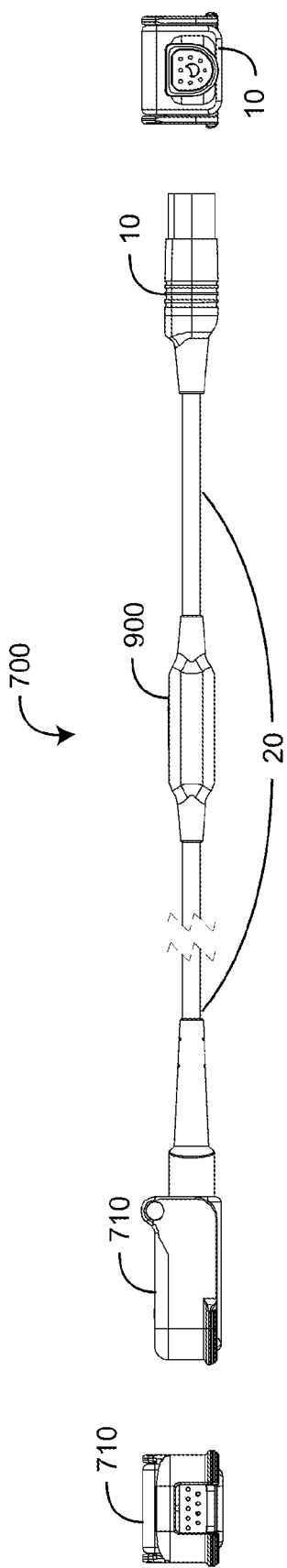

FIGS. 7A-B illustrate a sensor adapter cable embodiment 700 employing a DB9 sensor connector 710 and a D8 plug-in connector 10. A cable 20 interconnects the sensor connector 710 and the plug-in connector 10. A pod 900 integrated with the cable 20 contains a sensor adapter circuit 400 (FIG. 4) that insures electrical compatibility between a passive and an active ID 110 (FIG. 1) and a particular plug-in 130 (FIG. 1).

FIGS. 8A-C further illustrate a sensor adapter cable embodiment 700, showing the respective pinouts of the DB9 connector 710 and the D8 connector 10. Also shown are the corresponding cable 20 color-coded wires, inner shield and outer shield. Further shown are the sensor adapter circuit 400 connections relative to the connectors 10, 710 and cable 20 wires.

FIGS. 9A-B illustrate a pod 900 that splices the sensor adapter circuit 400 (FIG. 4) into the sensor adapter cable 20. The pod 900 has a overmold 910, a premold 920, a copper foil shield 930, a circuit board 940 and heat-shrink tubing 950. The circuit board 940 provides the sensor adapter circuit 400 (FIG. 4) described above. The board 940 is mounted to the cable 20 and electrically interconnected to the cable wires and outer shield, as described with respect to FIG. 4, above. The premold 920 is manufactured to envelop the circuit board 940 and spliced cable portion. The copper foil shield 930, if used, envelops the premold 920, and the overmold 910 envelops all of the pod 900 components.

Figure 11B:
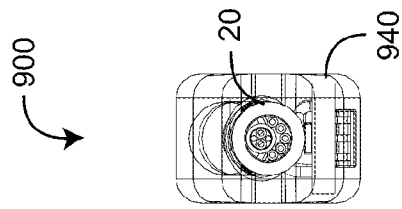
FIGS. 11A-C are transparent top, end and front views, respectively, of the pod.
Figure 11A:
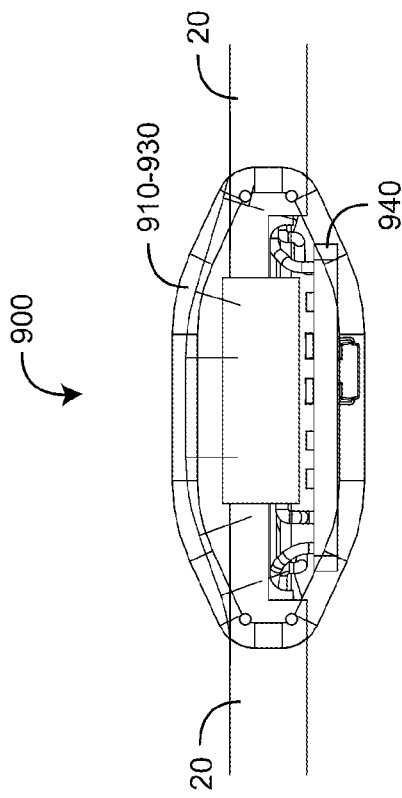
Figure 11C:
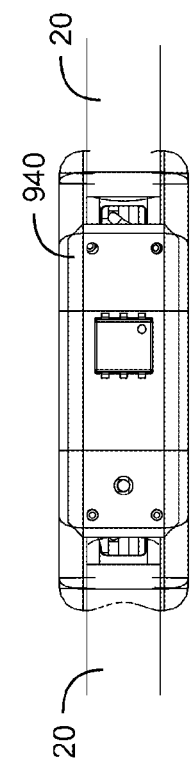

FIGS. 10A-D illustrate attachment of the circuit board 940 to the adapter cable 20. Shown is cable preparation (FIG. 10D) for splicing with the circuit board 940 (FIG. 10C). Also shown are preparation of the cable wires (FIG. 10B) and mounting of the circuit board 940 to the cable wires. FIGS. 11A-C further illustrates the assembled pod 900.

A sensor adapter cable has been disclosed in detail in connection with various embodiments. These embodiments are disclosed by way of examples only and are not to be construed as limiting the scope of this disclosure. One of ordinary skill in the art will appreciate many variations and modifications.

What is claimed is:

1. A sensor adapter cable provides medical personnel with the convenience of utilizing otherwise incompatible optical sensors with multiple blood parameter plug-ins to a physiological monitor, where the plug-ins each have keyed connectors that mechanically lock-out incompatible sensors in addition to readers that poll sensor identification components in each sensor so as to electrically lockout incompatible sensors, the sensor adapter cable comprising:
   a sensor connector that mechanically connects to a predetermined sensor and electrically communicates with a plurality of sensor electrical elements within the predetermined sensor;
   a plug-in connector that mechanically connects to a predetermined plug-in and electrically communicates with a plurality of plug-in electrical elements within the predetermined plug-in;
   an interconnection cable that mechanically attaches between and provides electrical communications between the sensor connector and the plug-in connector; and
   a pod, including a circuit board, incorporated within the interconnecting cable that electrically interfaces the sensor connector to the plug-in connector; wherein the pod includes both active and passive identification elements;
   wherein the circuit board comprises a first switch that, when closed, connects a resistor ID on the circuit board to the plug-in connector so as to enable a first plug-in attached to the plug-in connector to communicate with a sensor attached to the sensor connector, wherein the first switch is one of an n-channel or p-channel MOSFET;

wherein the circuit board comprises a second switch that, when closed, connects an EEPROM ID on the circuit board to the plug-in connector so as to enable a second plug-in attached to the plug-in connector to communicate with a sensor attached to the sensor connector, wherein the second switch is the other of an n-channel or p-channel MOSFET.

2. The sensor adapter cable according to claim 1 wherein the pod comprises:
   a cut in the interconnection cable that exposes a plurality of cable wire ends;
   the circuit board spliced to the cable wires ends;
   a pre-mold that encapsulates the cut, the circuit board, and the cable wire end; and
   an over-mold that envelopes the pre-mode so as to define the pod.

3. The sensor adapter cable according to claim 1 wherein the sensor adapter cable disconnects the resistor ID and the EEPROM ID when the first switch and the second switch are both open.

4. The sensor adapter cable according to claim 1 wherein the first switch turns on in response to a positive control signal from the first plug-in so as to switch in the resistor ID.

5. The sensor adapter cable according to claim 1 wherein the second switch turns on in response to a negative control signal from the second plug-in so as to switch in the EEPROM ID.

6. A method of using a sensor adapter cable for interfacing any of multiple physiological monitor plug-ins to any of multiple optical sensors comprising:
   providing an interface cable having a sensor connector on a first end and a plug-in connector on a second end, and incorporating a plurality of passive and active memory identifications (IDs) within the cable, wherein the passive ID is at least one resistive ID and the active ID is a memory ID;
   asserting a sensor ID read signal at the plug-in connector; and
   selecting a particular one of the IDs to present to the plug-in connector in response to the read signal using one of an n-type MOSFET or a p-type MOSFET for the resistive ID and using the other of an n-type MOSFET or a p-type MOSFET for the memory ID.

7. The method according to claim 6 further comprising isolating unselected IDs from the plug-in connector and the selected ID.

8. The method according to claim 7 wherein the n-type MOSFET and p-type MOSFET are responsive to the read signal so as to connect the selected ID and disconnect the remaining IDs.

9. The method according to claim 8 further comprising closing a first one of the n-type MOSFET or p-type MOSFET and opening a the other of the n-type MOSFET or p-type MOSFET so as to select either a resistive ID or a memory ID.

10. The method according to claim 8 further comprising opening both the n-type MOSFET and p-type MOSFET so that the sensor adapter cable functions as a patient cable.

11. The method according to claim 10 wherein the providing further comprises a circuit board with the n-type MOSFET and p-type MOSFET and IDs spliced between a portion of the interface cable conductors.

12. The method according to claim 11 the circuit board is encapsulated into a calibration pod portion of the interface cable.

13. A sensor adapter cable comprising:
   a plug-in connector means for connecting to a plug-in module for a physiological monitor;
   a sensor connector means for connecting to an optical sensor;
   an interface cable that mechanically and electrically interconnects the plug-in connector means and the sensor connector means; and
   a pod means integrated with the interface cable for allowing a plurality of sensors to connect to and be recognized by the plug-in module, the pod means including at least passive and active memory identifications (IDs);
   a switching means for selectively activating and isolating the IDs so that only a single ID is presented to the plug-in connector, wherein the switching means comprises one of an n-type MOSFET or a p-type MOSFET for the at least one of the IDs and the other of an n-type MOSFET or a p-type MOSFET for the at least another of the IDs.

14. The sensor adapter cable according to claim 13 further comprising a control means in communications with the plug-in connector means for making the switching means responsive to a ID read signal from the plug-in module.

15. The sensor adapter cable according to claim 14 wherein the pod means further comprises an encapsulation means for enclosing a circuit board within the pod means.

16. The sensor adapter cable according to claim 15 wherein the encapsulations means comprises:
   a premold of at least one of an epoxy, HDPE and PVC; and
   an overmold of medical grade PVC.

* * * * *

UNITED STATES PATENT AND TRADEMARK OFFICE
CERTIFICATE OF CORRECTION

| | | |
|---|---|---|
| PATENT NO. | : 9,138,180 B1 | Page 1 of 1 |
| APPLICATION NO. | : 13/100287 | |
| DATED | : September 22, 2015 | |
| INVENTOR(S) | : Coverston et al. | |

It is certified that error appears in the above-identified patent and that said Letters Patent is hereby corrected as shown below:

In the claims

Column 8, Line 7, claim 9, change "a the" to --the--.

Signed and Sealed this
Twenty-fourth Day of May, 2016

Michelle K. Lee
*Director of the United States Patent and Trademark Office*